(12) United States Patent
Bivens et al.

(10) Patent No.: US 7,568,380 B2
(45) Date of Patent: Aug. 4, 2009

(54) TURBINE VISCOMETER

(75) Inventors: Jason D. Bivens, Duncan, OK (US); James L. Davis, Marlow, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 204 days.

(21) Appl. No.: 11/592,521

(22) Filed: Nov. 3, 2006

(65) Prior Publication Data

US 2008/0105040 A1    May 8, 2008

(51) Int. Cl.
*G01N 11/14* (2006.01)
(52) U.S. Cl. .................. 73/54.28; 73/54.23; 73/54.32
(58) Field of Classification Search ............... 73/54.28, 73/54.35, 54.32, 54.33, 54.23, 54.25, 54.26, 73/54.27, 54.34
See application file for complete search history.

(56) References Cited

U.S. PATENT DOCUMENTS 3,256,737 A * 6/1966 Sipin ........................ 73/861.83
3,498,129 A * 3/1970 Bodge ..................... 73/861.352
3,575,052 A * 4/1971 Lenker ................... 73/861.352
4,067,230 A   1/1978 Ball ............................ 73/54.01

OTHER PUBLICATIONS

[Internet], [retrieved on Sep. 13, 2006], Brookfield Engineering, http://www.brookfieldengineering.com/products/viscometers.

* cited by examiner

*Primary Examiner*—Daniel S Larkin
*Assistant Examiner*—Tamiko D Bellamy
(74) *Attorney, Agent, or Firm*—John W. Wustenberg; McAfee & Taft

(57) ABSTRACT

A turbine viscometer for measuring the viscosity of fluid flowing through a conduit, such as a pipe or manifold. The viscometer has a viscosity turbine positionable in the pipe or manifold. The viscosity turbine has a central portion and a plurality of blades extending therefrom such that fluid flow does not induce any rotational movement of the viscosity turbine. The viscometer also has a drive device for rotating the viscosity turbine so that fluid drag on the viscosity turbine can be measured to determine the viscosity of the fluid. In one embodiment, the drive device creates a rotational magnetic field around the viscosity turbine so that it is rotated. In a second embodiment, the drive device is a drive turbine connected to the viscosity turbine and rotated by fluid flowing through the pipe or conduit.

12 Claims, 2 Drawing Sheets

TURBINE VISCOMETER

BACKGROUND OF THE INVENTION

1. Field of the Invention

The present invention relates to fluid viscometers for measuring the viscosity of fluid in a conduit such as pipe or manifold, and more particularly, to turbine viscometers that can provide a viscosity measurement of flowing fluid without the necessity of any mechanical penetration through the pipe or manifold.

2. Description of the Prior Art

The measurement of the viscosity of a fluid flowing in a pipe or other conduit is well known but can be problematic. Particularly difficult fluids to measure are fracturing fluids and gels used in fracturing of well formations. The viscosity of the fluid is, of course, measurable before it is pumped into the well, but this measurement is not always satisfactory because the viscosity of the fluid may change in the well. Heat and other well conditions may affect the fluid in ways that are not entirely predictable.

Therefore, it is desirable to be able to measure the viscosity of such fluids "on the fly" as the fluid is flowing through the pipe. Currently, there is no known in-line device which can be used for measuring full stream on most fracturing treatments. Current technology requires that the fluid be free of proppants, so any measurements taken are not accurate.

The present invention solves this problem by providing a turbine rotatable in the pipe such that the rotation of the turbine can be determined magnetically. The magnetic slip or drag on the turbine is a function of fluid shear in the fluid being measured, and this is proportional to viscosity. The turbine can be rotated by a rotating magnetic field external of the pipe or by a drive turbine which is rotated by the fluid flow. Electromagnets and pickups can be embedded in the wall of the pipe with no mechanical penetration therein.

SUMMARY OF THE INVENTION

The present invention is a turbine viscometer apparatus which can be directly or indirectly coupled to a drive means. The turbine viscometer is designed to provide real-time, in-line measurement of viscosity for a fluid being flowed in a pipe or manifold. The apparatus is independent of pressure and flow and minimizes the possibility of a malfunction due to contaminated or dirty fluids.

The fluid measuring apparatus may be described as comprising a viscosity turbine disposable in a conduit, a drive device for rotating the turbine and a measuring device for measuring fluid drag on the turbine, the drag being a function of the viscosity of the fluid in the conduit. The turbine has a central portion and a plurality of blades extending therefrom. The blades are adapted such that fluid flowing through the conduit induces no rotational movement of the turbine.

In one embodiment, at least a portion of the turbine is made of a magnetically influenced material, and the drive device induces a rotating magnetic field around the turbine. The measuring device comprises an electromagnet and measures the current flowing through the drive device.

In another embodiment, the drive device may be a drive turbine coupled to the viscosity turbine, the drive turbine having a central portion and a plurality of drive blades extending therefrom and adapted such that flow of fluid through the conduit induces rotation of the drive turbine. That is, the drive blades have a curvature that applies a rotational force to the drive turbine as a result of fluid flowing over the drive blades. The apparatus further comprises a coupling interconnecting the central portion of the viscosity turbine and the central portion of the drive turbine. In this embodiment, the measuring device comprises a magnetic pickup adjacent to the drive and viscosity turbines. The measuring device may be used to measure angular slip between the viscosity and drive turbines.

Stated in another way, the present invention is an apparatus for measuring fluid viscosity in a conduit that comprises a turbine disposable in the conduit, wherein the turbine has a central portion and a plurality of blades extending therefrom, at least a portion of the turbine being made from a magnetically influenced material. The blades are adapted such that fluid flowing through the conduit induces no rotational movement of the turbine. The apparatus further comprises a drive device for creating a rotating magnetic field around the turbine such that the turbine is rotated and fluid drag is created on the blades of the turbine and a measuring device for measuring the torque required to rotate the turbine.

Stated in still another way, the present invention is an apparatus for measuring fluid viscosity in a conduit comprising a viscosity turbine disposable in the conduit, a drive turbine disposable in the conduit and a measuring device for measuring angular slip between the viscosity and drive turbines. The drive turbine is coupled by a rotationally flexible coupling to the viscosity turbine and has a central portion and a plurality of drive blades extending therefrom. The drive blades are adapted such that flow of fluid through the conduit induces rotation of the drive turbine. The measuring device may comprise a magnetic pickup that receives pulses from blades moving adjacent thereto.

Numerous objects and advantages of the invention will become apparent as the following detailed description of the preferred embodiments is read in conjunction with the drawings illustrating these embodiments.

BRIEF DESCRIPTION OF THE DRAWINGS

FIG. 3 illustrates a second embodiment of the turbine viscometer wherein the viscometer is directly coupled to a drive turbine.

DESCRIPTION OF THE PREFERRED EMBODIMENTS

Figure 1:
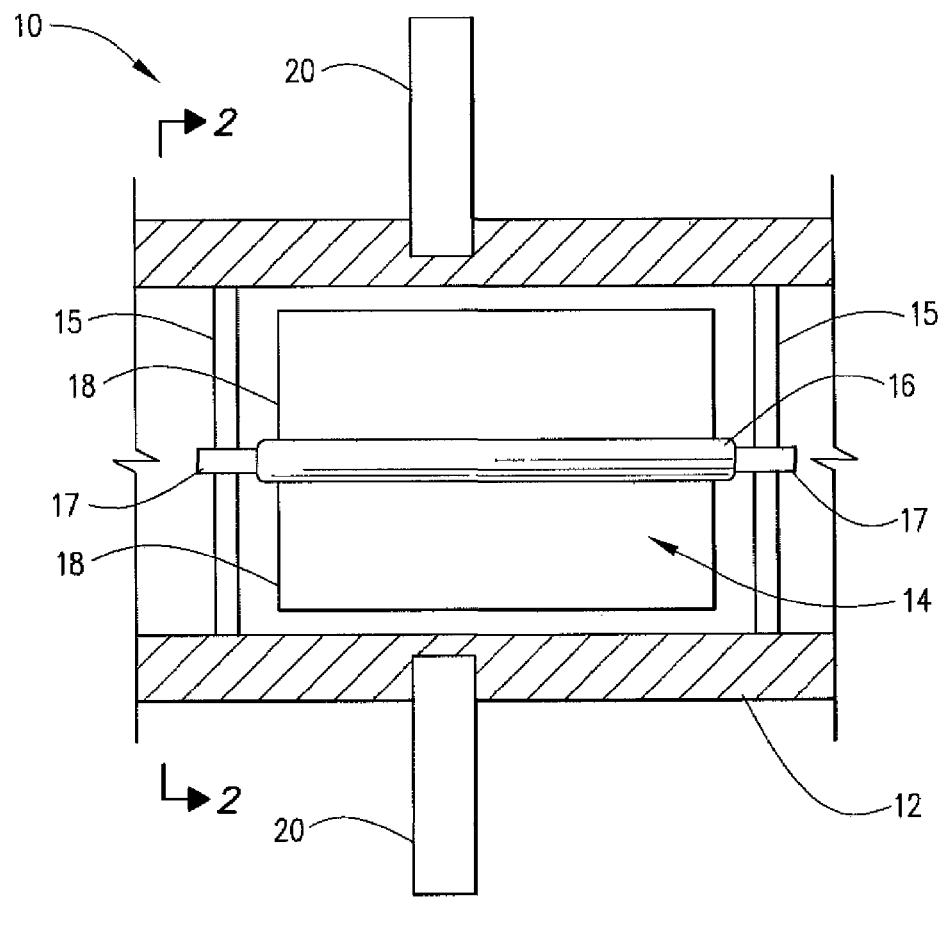
FIG. 1 shows a first embodiment of the turbine viscometer of the present invention wherein the viscometer is indirectly coupled to a magnetic drive system.
Figure 2:
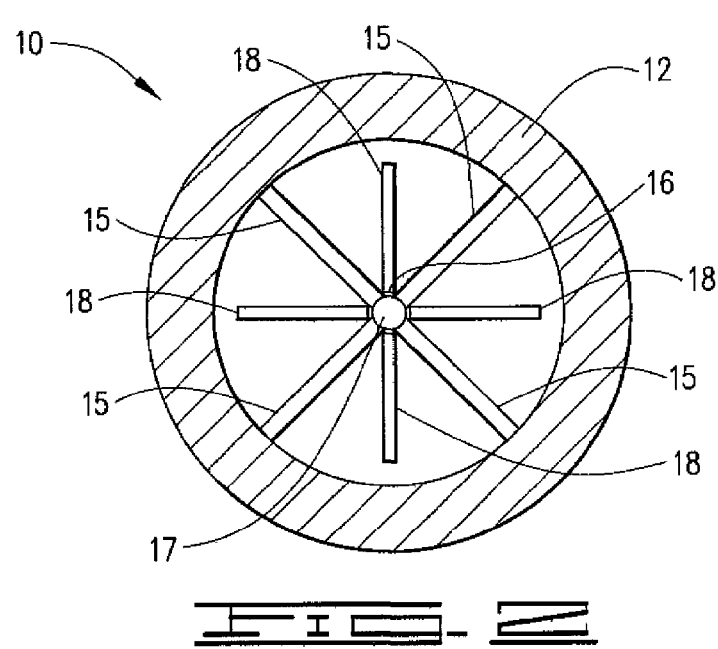
FIG. 2 is a cross section taken along lines 2-2 in FIG. 1.
Figure 2:
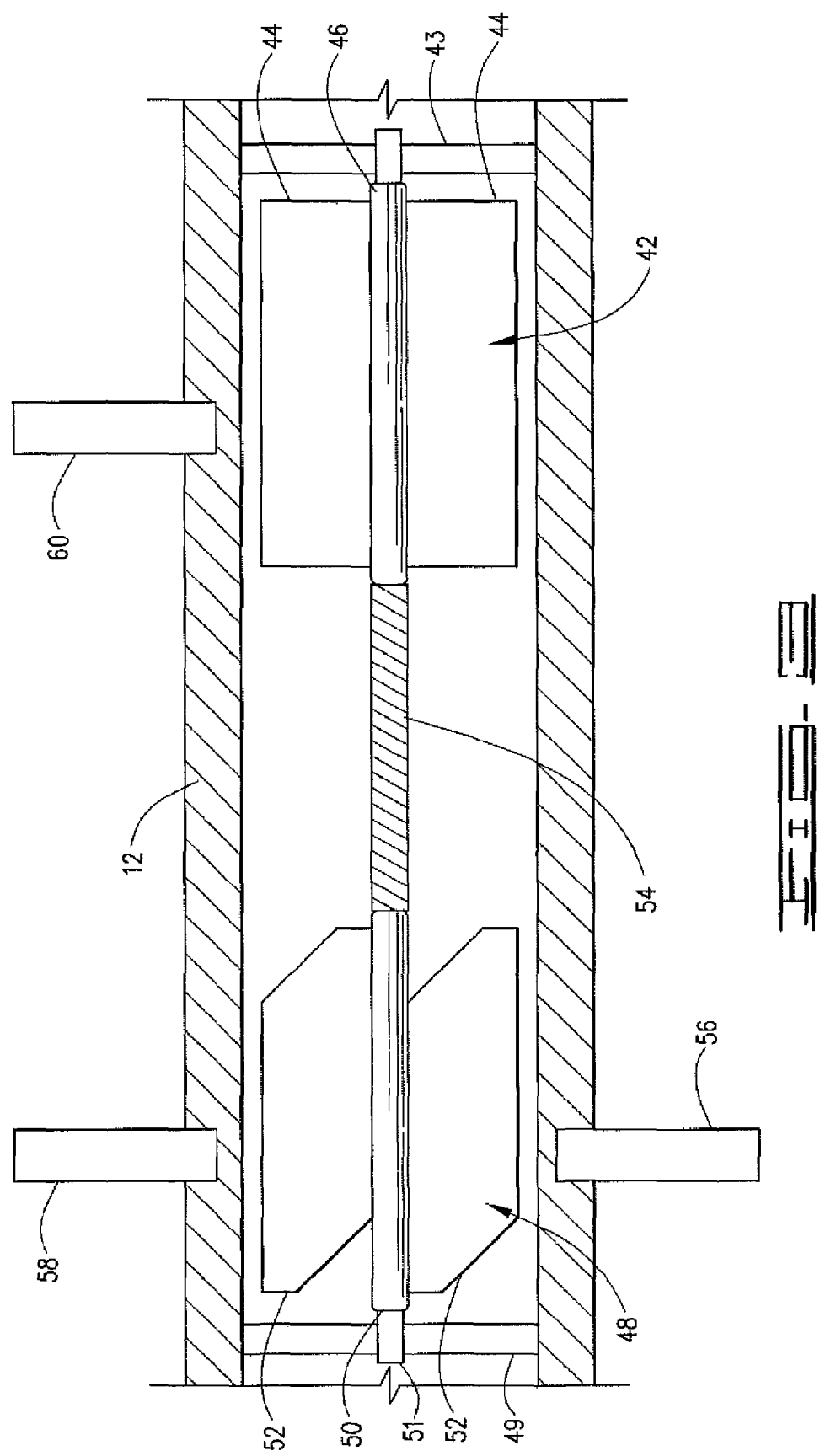

Referring now to the drawings, and more particularly to FIGS. 1 and 2, a first embodiment of the turbine viscometer apparatus of the present invention is shown and generally designated by the numeral 10. Apparatus 10 is shown in an operating position in a conduit, such as a pipe or manifold 12.

Apparatus 10 comprises a viscosity turbine 14 mounted on supports 15 that are connected to the inner surface of pipe 12.

Turbine 14 is made at least partially of a magnetically influenced material, such as a ferrous metal. Turbine 14 has a central portion 16 with a plurality of radial blades 18 extending therefrom. Central portion 16 is rotatably mounted on bearings 17 on supports 15. In this way, turbine 14 is adapted to spin freely within pipe 12. Blades 18 extend longitudinally in pipe 12 and are thus parallel to the flow of fluid in the pipe. Blades 18 have zero pitch with respect to the flow of fluid through pipe 12. It will thus be seen by those skilled in the art that turbine 14 is designed such that the fluid flow induces no rotational movement of the turbine. Four blades 18 are illustrated, but the invention is not intended to be limited to any specific number of blades or any particular configuration of supports 15.

A permanent or electrical magnetic-induced magnetic field is created around turbine 14 by a means such as a plurality of electromagnets or windings 20. Electromagnets 20 are attached to pipe 12 or embedded in the wall thereof without any mechanical penetration of the pipe.

In operation of first embodiment apparatus 10, electromagnets 20 are used to induce a magnetic field around turbine 14. Because the material of turbine 14 is magnetically influenced, it rotates within pipe 12 by the magnetic field. The torque required to rotate turbine 14 is measured, and this reading is proportional to the viscosity of the fluid in which the turbine is rotating. Torque can be measured by the amount of current (which creates magnetic flux) required in windings or electromagnets 20 to keep the rotor at a synchronous speed. The construction of the windings/magnets is generally similar to stator windings, such as those found in electric motors known in the art.

Referring now to FIG. 3, a second embodiment of the turbine viscometer apparatus of the present invention is shown and generally designated by the numeral 40. Apparatus 40 is also shown in an operating position in pipe or manifold 12.

Apparatus 40 comprises a viscosity turbine 42 mounted on support 43 connected to the inner surface of pipe 12. Viscosity turbine 42 may also be referred to as driven turbine 42. Viscosity turbine 42 is made at least partially of a magnetically influenced material and is similar to turbine 14 in first embodiment apparatus 10. Viscosity turbine 42 has a central portion 44 with a plurality of radial blades 46 extending therefrom. Central portion 44 of viscosity turbine 42 is rotatably mounted on a bearing 45 on support 43, and thus is adapted to spin freely within pipe 12. Blades 46 extend longitudinally in pipe 12 and are thus parallel to the flow of fluid in the pipe. Blades 46 have zero pitch with respect to the flow of fluid through pipe 12. It will thus be seen by those skilled in the art that viscosity turbine 42 is designed such that the fluid flow induces no rotational movement of viscosity turbine 42.

A drive turbine 48 is mounted on a support 49 in pipe 12 and spaced from viscosity turbine 42. Drive turbine 48 has a central portion 50 with a plurality of drive blades 52 extending therefrom. Central portion 50 of drive turbine 48 is rotatably mounted on a bearing 51 on support 49, and thus is adapted to spin freely within pipe 12. Drive blades 52 have a curvature or pitch such that the drive blades are adapted so the fluid flow through pipe 12 induces rotation of drive turbine 48. In other words, the flowing fluid engaging drive blades 52 causes a rotational force to be applied to drive turbine 48. The invention is not intended to be limited to any specific number of drive blades 52.

Central portion 50 of drive turbine 48 is coupled to central portion 44 of viscosity turbine 42 by a coupling 54 such that the rotation of drive turbine 48 due to fluid flow results in rotation of viscosity turbine 42. Coupling 54 is flexibly designed or made of a flexible material to flex in an angular direction thereby allowing rotational angular displacement between drive turbine 48 and viscosity turbine 42. This angular displacement is dependent on applied torque created by drag from the viscosity turbine independent of flow. This angular displacement or "slip" is a function of viscosity. The rotational speed of viscosity turbine 42 and drive turbine 48 may be controlled by a variable magnetic drag induced on the drive turbine by an electromagnet 56. This slip is detected by the different readings from a drive turbine pickup 58 and a viscosity turbine pickup 60. Electromagnet 56 and pickups 58 and 60 are connected to pipe 12 or embedded in the wall thereof.

For example, in an air stream, viscosity turbine 42 and drive turbine 48 will turn together because there is very little resistance to cause the viscosity turbine to rotate with the drive turbine. In a viscous/thick fluid, the rotation of viscosity turbine 42 will be inhibited because of shearing of the fluid while drive turbine 48 continues to try to spin. This reluctance of viscosity turbine 42 to spin will cause it to "lag" behind drive turbine 48. If flexible coupling 54 is designed for the ranges of induced drag (torque), viscosity turbine 42 and drive turbine 48 will be out of phase. That is, the drive turbine will lead the viscosity turbine. This phase difference is easily measured with magnetic pickups, such as drive turbine pickup 58 and viscosity turbine pickup 60 that give a pulse with each passing blade. If viscosity turbine 42 and drive turbine 48 are set up with the blades initially in line, then the pulses will be simultaneous. As the viscosity increases, viscosity turbine 42 will start to lag behind drive turbine 48, and so the pulses from the blades on the viscosity turbine will occur after those on the drive turbine. How much these pulses lag behind those of the drive will relate to the viscosity of the fluid.

It will be seen, therefore, that the turbine viscometer of the present invention is well adapted to carry out the ends and advantages mentioned as well as those inherent therein. While presently preferred embodiments of the invention have been shown for the purposes of this disclosure, numerous changes in the arrangement and construction of parts may be made by those skilled in the art. All such changes are encompassed within the scope and spirit of the appended claims.

What is claimed is:

1. An apparatus for measuring fluid viscosity in a conduit, comprising:
   a viscosity turbine disposable in the conduit, wherein the viscosity turbine has a central portion and a plurality of blades extending therefrom, and the blades are adapted such that fluid flowing through the conduit induces no rotational movement of the viscosity turbine;
   a drive device for rotating the viscosity turbine; and
   a measuring device for measuring fluid drag on the viscosity turbine, wherein the drag is a function of the viscosity of the fluid in the conduit.

2. The apparatus of claim 1 wherein:
   the drive device is a drive turbine coupled to the viscosity turbine; and
   the drive turbine has a central portion and a plurality of drive blades extending therefrom and adapted such that flow of fluid through the conduit induces rotation of the drive turbine.

3. The apparatus of claim 2 further comprising a coupling interconnecting the central portion of the viscosity turbine and the central portion of the drive turbine.

4. The apparatus of claim 2 wherein the measuring device measures angular slip between the viscosity and drive turbines.

5. An apparatus for measuring fluid viscosity in a conduit, comprising:
   a turbine disposable in the conduit, wherein the turbine has a central portion and a plurality of blades extending therefrom, the blades are adapted such that fluid flowing through the conduit induces no rotational movement of the turbine, and at least a portion of the turbine is made from a magnetically influenced material;

a drive device for creating a rotating magnetic field around the turbine such that the turbine is rotated and fluid drag is created on the blades of the turbine; and a measuring device for measuring the torque required to rotate the turbine.

6. The apparatus of claim 5 wherein the drive device comprises an electromagnet.

7. The apparatus of claim 5 wherein the measuring device measures current flowing through the drive device.

8. An apparatus for measuring fluid viscosity in a conduit, comprising:

a viscosity turbine disposable in the conduit, wherein the viscosity turbine has a central portion and a plurality of blades extending therefrom, and the blades are adapted such that fluid flowing through the conduit induces no rotational movement of the viscosity turbine, wherein at least a portion of the viscosity turbine is made of a magnetically influenced material;

a drive device for rotating the viscosity turbine, wherein the drive device induces a rotating magnetic field around the viscosity turbine; and a measuring device for measuring fluid drag on the viscosity turbine, wherein the drag is a function of the viscosity of the fluid in the conduit.

9. An apparatus for measuring fluid viscosity in a conduit, comprising:

a viscosity turbine disposable in the conduit, wherein the viscosity turbine has a central portion and a plurality of blades extending therefrom, and the blades are adapted such that fluid flowing though the conduit induces no rotational movement of the viscosity turbine;

a drive device for rotating the viscosity turbine, wherein the drive device is a drive turbine coupled to the viscosity turbine, the drive turbine having a central portion and a plurality of drive blades extending therefrom and adapted such that flow of fluid through the conduit induces rotation of the drive turbine; and a measuring device for measuring fluid drag on the viscosity turbine, wherein the drag is a function of the viscosity of the fluid in the conduit and the measuring device comprises a magnetic pickup adjacent to the drive and viscosity turbines.

10. An apparatus for measuring fluid viscosity in a conduit, comprising:

a viscosity turbine disposable in the conduit wherein the viscosity turbine has a central portion and a plurality of blades extending therefrom, and the blades are adapted such that fluid flowing though the conduit induces no rotational movement of the viscosity turbine;

a drive device for rotating the viscosity turbine, wherein the drive device is a drive turbine coupled to the viscosity turbine, the drive turbine having a central portion and a plurality of drive blades extending therefrom and adapted such that flow of fluid though the conduit induces rotation of the drive turbine;

a flexible coupling interconnecting the central portion of the viscosity turbine and the central portion of the drive turbine; and a measuring device for measuring fluid drag on the viscosity turbine, wherein the drag is a function of the viscosity of the fluid in the conduit.

11. The apparatus of claim 8 wherein the measuring device comprises an electromagnet.

12. The apparatus of claim 8 wherein the measuring device measures the current flowing through the drive device.

* * * * *